United States Patent [19]

Engel

[11] Patent Number: 4,524,087
[45] Date of Patent: Jun. 18, 1985

[54] CONDUCTIVE ADHESIVE AND BIOMEDICAL ELECTRODE

[75] Inventor: Michael R. Engel, White Bear Lake, Minn.

[73] Assignee: Minnesota Mining and Manufacturing Company, St. Paul, Minn.

[21] Appl. No.: 514,950

[22] Filed: Jul. 18, 1983

Related U.S. Application Data

[62] Division of Ser. No. 114,565, Jan. 23, 1980, abandoned.

[51] Int. Cl.³ .................. A01N 1/02; B05D 3/02; B05D 3/06; A61B 5/04
[52] U.S. Cl. .................. 427/2; 128/639; 128/640; 128/641; 128/798; 128/802; 427/54.1; 427/388.2
[58] Field of Search .................. 128/639–641, 128/798, 802; 427/2, 54.1, 388.2

[56] References Cited

U.S. PATENT DOCUMENTS

| | | |
|---|---|---|
| 3,587,565 | 6/1971 | Tatoian .................. 128/640 |
| 3,805,769 | 4/1974 | Sessions .................. 128/640 |
| 3,812,861 | 5/1974 | Peters .................. 128/640 |
| 3,911,906 | 10/1975 | Remhold .................. 128/640 |
| 3,998,215 | 12/1976 | Anderson et al. .................. 128/640 |
| 4,008,721 | 2/1977 | Burton .................. 128/640 |
| 4,016,869 | 4/1977 | Reichenberger .................. 128/640 |
| 4,066,078 | 1/1978 | Berg .................. 128/640 |
| 4,094,822 | 6/1978 | Kater .................. 128/640 |
| 4,125,110 | 7/1978 | Hymes .................. 128/640 |
| 4,273,135 | 6/1981 | Larimore et al. .................. 128/640 |
| 4,352,359 | 10/1982 | Larimore et al. .................. 128/640 |
| 4,391,278 | 7/1983 | Cahalan et al. .................. 128/640 |

FOREIGN PATENT DOCUMENTS 2814061 10/1978 Fed. Rep. of Germany ...... 128/783

Primary Examiner—Michael R. Lusignan
Attorney, Agent, or Firm—Donald M. Sell; James A. Smith; Carolyn A. Bates

[57] ABSTRACT

A biomedical electrode having a conductive adhesive thereon which is derived from an essentially solventless process. The resulting adhesive is characterized in that it is a swellable, dermally-nonirritating conformable, coadhesive, ionic, hydrophilic polymer.

17 Claims, 4 Drawing Figures

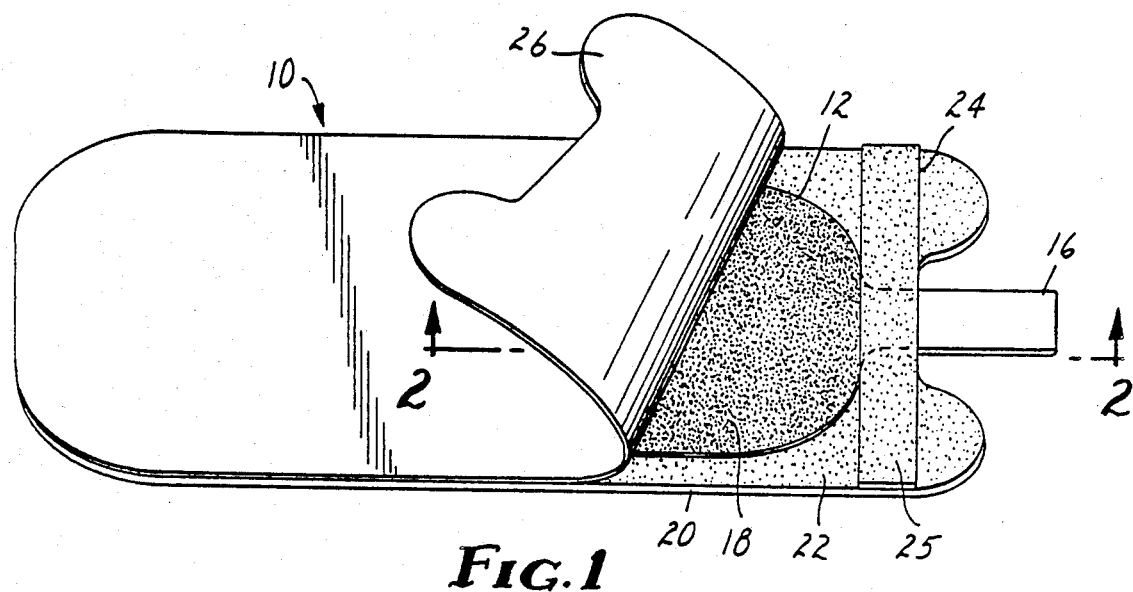
FIG. 1
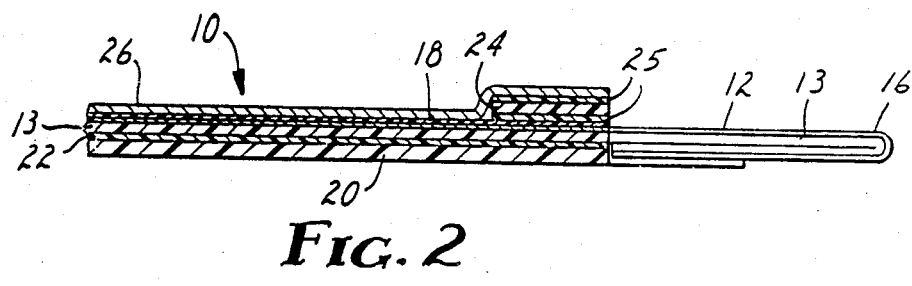
FIG. 2
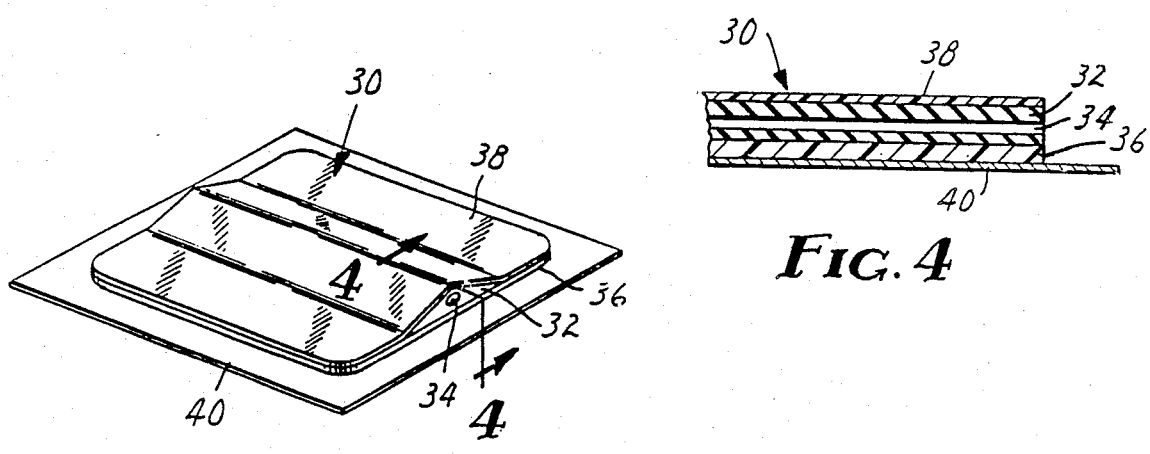
FIG. 3
FIG. 4

CONDUCTIVE ADHESIVE AND BIOMEDICAL ELECTRODE

This is a division of application Ser. No. 114,565 filed Jan. 23, 1980, now abandoned.

This invention relates to a conductive adhesive especially useful in biomedical electrodes used to establish an electrical connection between the skin of the human anatomy and an electromedical apparatus, such as a high impedance electromyograph, electrocardiograph, electrical neurostimulator for pain relief, and the like. More particularly it relates to a conductive adhesive for use in so-called "dry" bioelectrodes which do not require the use of messy creams or gels to enhance conductivity between the skin and the electrode plate.

A variety of disposable biomedical electrodes are known in the art. Generally, they comprise a metallic electrode plate adapted for connection to a lead wire which is, in turn, attached to the electromedical apparatus. Typically, a paste, cream, or gel which contains ionic material is relied upon to conduct the electric current and improve the electrical connection between the skin of the patient and the electrode plate. An adhesive tape is commonly used to adhere the entire apparatus to the skin. Examples of electrodes of this general type are described in U.S. Pat. Nos. 3,587,565 and 3,805,769.

The conductive pastes, creams, or gels used in these prior art biomedical electrodes are unpleasant to use, sloppy, and often irritating to the skin particularly when the skin is cleaned and abraded prior to application of the electrode. Since these electrodes all contain water as the major ingredient to solvate the ions present and function as a medium through which the solvated ions migrate, they require elaborate packaging to prevent loss of water prior to use. Furthermore, they leave a residue on the skin after removal of the electrode which requires cleanup. A further disadvantage of the electrodes of the conductive paste, cream, and gel types is that they may develop an over-potential in defibrillation procedures unless the surface of the electrode plate is of expensive silver/silver chloride.

To overcome many of the problems asscociated with so called "wet" electrodes, biomedical electrodes having an integrally formed metal snap connector have been proposed which utilize "dry" conductive material. U.S. Pat. Nos. 4,008,721 and 3,911,906 disclose biomedical electrodes utilizing adhesives impregnated with conductive particles. These adhesives serve the dual purpose of enhancing conductivity with the skin and securing the electrode to the skin. Although avoiding the sloppiness and packaging problems associated with gels and pastes, such electrodes generally do not provide satisfactory electrical connection to the skin because the presence of the conductive filler results in a high signal-to-noise ratio and is deleterious to adhesion. Generally, the use of nonhomogeneous conductive formulations in bioelectrodes has been found to give rise to noisy electrical signals. It is speculated that dispersed metal or salt particles in a binder matrix form a discontinuous, electrically conductive path which develops random, nonuniform electrical fields between particles which cause noise.

Another biomedical electrode used for transcutaneous electrical neural stimulation (TENS) disclosed in U.S. Pat. No. 4,125,110 utilizes a natural polymer, namely, gum karaya, for securing the electrode to skin. Gum karaya is a complex polysaccharide combined with certain metallic cations, such as sodium, potassium, calcium, or magnesium. The gum does not dissolve but swells in water to a paste-like gel (Kirk-Othmer, Encyclopedia of Chemical Technology, Vol. 10, 1966). Because natural polymers originate in nature where soil and climatic conditions are variable, and the conditions under which they are collected and processed are variable, there is a great inconsistency in the physical and chemical properties of natural polymers and in the amount of impurities present. Such inconsistency leads to variations in the electrical performance of biomedical electrodes made from natural polymers. This variation in electrical performance cannot be tolerated in biomedical electrodes where consistent electrical properties are important for signal reception. Furthermore, the natural polymers are undesirable because they generally support undesirable microbial growth and have the potential for creating adverse skin sensitivites including allergenic and antigenic reactions (Merck Index, 8th Edition, 1969, page 598).

Other "dry" electrodes are also known. U.S. Pat. No. 3,812,861 teaches a grounding electrode consisting of a flexible sheet of paperboard coated on both sides with a conductive foil joined electrically together and a means for tightening the device around a limb. Such electrodes having a metal-to-tissue interface are undesirable because of the bio-incompatability of most metals and the difficulty of obtaining adequate conformability with the body surface. U.S. Pat. No. 4,066,708 has addressed this metal bio-incompatability by placing a conductive layer on the skin contacting surface of the metal. The disclosed conductive formulations consist of suspension polymers which require numerous process steps, e.g. removal of solvents, which would tend to substantially increase the cost associated with the manufacturing of the electrode.

Another conductive adhesive has been called to applicant's attention which is a synthetic hydrophilic polymer containing at least 5 mole percent of monomer units containing salts of a carboxylic acid, see "Biomedical Electrode," U.S. patent application Ser. No. 940,734 filed Sept. 8, 1978 and owned by the same assignee as the present application.

The biomedical electrode and the conductive adhesive according to the present invention offer several advantages over the previously described biomedical electrodes. First, the present electrode by virtue of its dry conductive material eliminates messy gels, creams or pastes. Secondly, the conductive material is formed by an essentially solventless process in substantially its final form. This can be done in situ on a releasable surface for a later transfer to the electrode plate or directly on the electrode plate which eliminates the need for an additional transfer step. Neither of the aforementioned formation methods require process steps which are associated with the removal of solvent from suspension polymer formulations. Thirdly, the resultant conductive material which is formed has homogeneously dispersed therein free ions which minimize the potential for the formulation of nonuniform fields which are associated with dispersed metal or salt particles in binder matrices.

According to the present invention, there is provided an essentially dry disposable biomedical electrode comprising an electrode plate having a first surface and a second surface. The electrode plate has means for electrical connection to a lead wire of an electro-medical device. The second surface of the electro-plate contains a swellable non-soluble conductive material for enhancing the electrical connection with the skin. The conductive material is a polymer which is synthetic, dermally-nonirritating, conformable, cohesive, ionic and hydrophilic. The conductive material is formed from an essentially solventless process in situ on the electrode plate or a transfer sheet. The process involves first forming an adhesive precursor comprised of (1) a water-soluble polyhydric alcohol which is a liquid at room temperature; (2) an ionic unsaturated free radically polymerizable material which is soluble in the aforesaid polyhydric alcohol; (3) a free radical initiator which is soluble in the aforesaid polyhydric alcohol; and (4) a crosslinking agent of a multifunctional unsaturated free radically polymerizable material. To enhance the processing of the conductive layer of the present invention the precursor may also contain at least one non-ionic unsaturated free radically polymerizable comonomer which is soluble in the polyhdyric alcohol.

The term "solventless" is used herein to mean that there are essentially no materials present in the precursor which are not present in the final composition of the electrically conductive adhesive. Stated another way, when the polymerization of the precursor is complete and the adhesive is ready for use, at least 99% of the starting materials are still present.

The term "hydrophilic" is used herein to mean the conductive adhesive will absorb some water.

The term "conformable" as used herein refers generally to the compliance of the conductive material. It must be sufficiently compliant to conform to the surface of the skin beneath the electrode plate to provide a high surface area of contact between the skin and the electrode plate.

The term "cohesive" refers to the internal integrity of the conductive material. Generally, the conductive material is film-forming and must be more cohesive than adhesive to the skin so that, when the electrode is removed from the skin, the conductive layer remains intact and does not leave an onjectionable residue.

The term "swellable" refers to imbibing of solvents by the polymer matrix with a concomitant increase in the volume of the polymer matrix.

The electrically conductive material is derived from the essentially solventless process of polymerizing the precursor of which one component is the water-soluble polyhydric alcohol. The polyhydric alcohol is water-soluble and a liquid at room temperature, e.g., approximately 20° C. The polyhydric alcohol is present in the precursor in amounts of from 10 to 90 parts per weight of the precursor, with 50 to about 70 being preferred. Examples of useful polyhydric alcohols are propylene glycol, 1,2,4 Butane triol and glycerol, with the latter being preferred. One skilled in the art will recognize that a mixture may be prepared of polyhdyric alcohols which are not normally liquid at room temperature and those that are liquid to form a useful polyol. One skilled in the art would also recognize that the dihydric alcohol, ethylene glycol may be useful in the present invention but may cause dermal reactions which limit its utility.

As stated above, the precursor is also comprised of the unsaturated free radically polymerizable material which is soluble in the polyhydric alcohol. This material may be a monomer or comonomer. These monomers or comonomers are present in the precursor in amounts of 90 to 10 parts by weight of the precursor. Of the amount of unsaturated monomer or comonomers which are present in the precursor, at least 10 parts by weight is ionic. This ionic portion is preferably anionic and present in 30 parts by weight of the unsaturated monomer or comonomer. Examples of ionic comonomers are salts of $\alpha,\beta$-unsaturated carboxylic acids such as potassium acrylate or sodium methacrylate. Examples of useful non-ionic comonomers of free radically polymerizable monomers which are soluble in the polyhydric alcohol are acrylic acid, methacrylic acid and hydroxyethyl methacrylate.

The precursor is further comprised of 0.1 to 5 parts by weight per 100 parts of the unsaturated material of a crosslinking agent of a multifunctional unsaturated free radically polymerizable material. Examples are triethylene-glycol-bis-methacrylate, ethyleneglycol-bis-methacrylate, bisacrylamide, and triethyleneglycol-bis-acrylate, with the former being preferred in amounts from about 0.75 to about 1.5 parts.

The initiation of the polymerization within the precursor is facilitated by the presence of at least 0.1 part by weight per 100 parts of the unsaturated material of a free radical initiator which is soluble in the polyhydric alcohol. The initiator may be of the thermal or photo class. The actual selection is dependent on the monomers and the polyhydric alcohol. Examples of useful thermal initiators are benzoyl peroxide, azobisisobutyronitrile Di-t-butyl peroxide and Cumyl peroxide. Examples of useful photoinitiators are disclosed in the article Photoinitiators—An Overview by G. Berner et al in the Journal of Radiation Curing (Apr. 1979), pp. 2 through 9. The preferred photoinitiator is benzildimethylketal.

It will be recognized by one skilled in the art that other additives (e.g. tackifiers, such as polyacrylic acid) may be added to the precursor without departing from the spirit of the invention.

The essentially solventless precursor can be coated onto the electrode plate or transfer sheet and, depending on the free radical initiator, exposed to either heat or actinic radiation which results in the formation of an electrically conductive pressure-sensitive adhesive. The precursor may also be exposed to electron beam radiation to facilitate the crosslinking. Because the adhesive is crosslinked after it has been coated onto the electrode plate or a transfer sheet, a continuous, covalently-bonded network is formed through the adhesive coating.

A better understanding of the present invention will be obtained with reference to the accompanying drawing wherein like numbers refer to like parts and in which:

FIG. 1 is a perspective view of a grounding plate biomedical electrode of the present invention;

FIG. 2 is a sectional view of the biomedical electrode of the present invention through line 2—2 of FIG. 1;

FIG. 3 is a perspective view of a TENS biomedical electrode of the present invention; and FIG. 4 is a sectional view of the alternative embodiment of the biomedical electrode of FIG. 3 through line 4—4.

Referring to FIGS. 1 and 2, a grounding plate electrode 10 is depicted. The electrode is comprised of an electrode plate 12 having a first surface and a second skin-contacting surface and is constructed from an electrically conductive material such as stainless steel, silver, nickel or the like, compressed carbon or graphite, or a metal-coated plastic, fabric, or conductive plastic material. The preferred material for use as electrode plate 12 is aluminum. When aluminum is utilized, it is preferred that the first surface is coated with a polyester backing 13 to facilitate handling. The electrode plate has means associated therewith for electrical connection to a lead wire which is, in turn, connected to an electromedical device. In electrode 10 the means for electrical connection to a lead wire is illustrated by connector tab 16. Connector tab 16 may be adapted to fit an electromedical connecting clip which is well known to the medical art, e.g., U.S. Pat. No. 4,061,408, or equipped with a permanent lead wire (not shown). The skin-contacting surface of the electrode plate, i.e., second surface, is coated with a layer 18 of conductive material to be described below. Layer 18 is generally between about 5 to about 100 mils (0.12 mm to 2.54 mm) thick with approximately 10 mil (0.25 mm) being preferred. Overlying the polyester backing 13 and extending outward from the periphery thereof is a backing 20. Backing 20 aids in holding the electrode securely to the skin of the patient. Backing 20 is preferably made of a closed cell foam with an adhesive coating 22. The backing may be constructed from a vinyl foam tape sold as "Microfoam ™" brand surgical tape by 3M Company, St. Paul, Minn. Another is a closed cell polyethylene foam, sold as "Volara ™" brand foam by the Voltex Corporation of Lawrence, Mass. The adhesive 22 may be of the type disclosed in U.S. Pat. No. 2,973,286. An insulating strip 24 of polyethylene may be added if it is believed that the connector tab 16 is in need of additional insulation at the portion nearest the means for external electrical connection. Optionally, insulating strip 24 may have a double sided adhesive coating 25 of material similar to that of adhesive layer 22 which would allow strip 24 to aid in the securing of the electrode to the patient. An optional release liner 26 may be attached to the adhesive-coated surfaces of the electrode 10 in order to preserve the adhesive character until ready for use. Such release liners are well known to the art.

The present invention contemplates the use of the novel solventless process for construction of an alternative biomedical electrode construction similar to that disclosed in U.S. patent application Ser. No. 64,576 filed by Frank C. Larimore on Aug. 7, 1979, which is a continuation-in-part of his U.S. patent application Ser. No. 22,469, filed Mar. 21, 1979. As shown in FIGS. 3 and 4, alternative biomedical electrode 30 (a TENS electrode) is comprised of an electrode plate 32 of a carbon-impregnated silicone rubber, i.e., SE 7600 available from the General Electric Company, Waterford, N.Y. In electrode 30 the means for electrical connection to a lead wire is illustrated by female receptor 34. Female receptor 34 is adapted to fit a male pin lead of a connector. The second skin-contacting surface of electrode plate 32 is positioned onto a layer 36 of conductive material, described hereinabove, which had previously been formed on a transfer surface. In contrast to biomedical electrode 10, the layer 36 extends out to the outer periphery of a backing 38. Layer 36 is generally between 25 and 100 mils (0.63 mm and 2.54 mm). The electrode 30 is also optionally provided with a protective release liner 40. Release liner 40 protects the conductive layer from contamination prior to use.

A better understanding of the process of the present invention may be obtained from the following non-limiting examples:

EXAMPLE I

Preparation of adhesive precursor

Triethyleneglycol-bis-methacrylate (0.1 g) and 0.1 gram of Irgacure 651 (a benzildimethylketal produced by Ciba-Geigy) were dissolved in 25 grams of acrylic acid. This solution was added to 50 grams of glycerol. The mixture was stirred and a solution of 7 grams of potassium hydroxide in water (10 ml) was added. The resulting warm solution was cooled to room temperature before being used for coating.

The cooled adhesive precursor was knife coated onto an aluminum substrate consisting of a ½ mil. aluminum foil which had been laminated to a 178 mil. polyester backing. The resulting coating thickness was 6.7 mils (0.17 mm).

The coated substrate was then passed through a 3 foot inert chamber ($N_2$ atmosphere) under a bank of UV lights consisting of thirty 18-inch "black light" tubes for one minute which resulted in the polymerization of the coating. One-inch strips of the aluminum-laminate with polymerized coating were allowed to equilibrate for one week at 5%, 50% and 80% relative humidity (R.H.) and 74° F. 5% R.H. was obtained by storing the sample in a bell jar over Drierite ($Na_2SO_4$ sold by W. A. Hammond Drierite Co. of Xenia, Ohio) 50% R.H. was obtained by storing in a room with controlled humidity. 80% R.H. was obtained by storing the samples in a bell jar over saturated $(NH_4)_2SO_4$ solution. After equilibrating for one week the samples were tested for conductivity. The impedance (Z) in Ohms ($\Omega$) to steel and phase angle ($\theta$) were measured using a two-square-inch piece of stainless steel and a HP 4800 beta impedance meter (manufactured by Hewlett Packard of Palo Alto, Calif.) with the frequency set at 500 KHz. The adhesion to steel (180° peel) in ounces per inch (oz/in) was obtained by placing a one inch wide strip of adhesive on a stainless steel plate. The strip was then rolled twice with a 2½ lb. roller. The force required to peel off the adhesive at 180° angle was measured using a Model #1122 Instron ™, manufactured by the Instron Corporation of Canton, Mass.

The results were:

| % R.H. | Impedance Z (Ω) | Adhesion to Steel (oz/in) |
|---|---|---|
| 5% | 21 | 5 no transfer of adhesive observed |
| 50% | 1.6 | 4.5 no transfer |
| 80% | 1.4 | 4.5 transfer |

EXAMPLES II THROUGH XI

Examples II through XI were produced in accordance with the procedure of Example I except the amounts of the components were varied. The amount of each component used and test results obtained are tabulated below.

EXAMPLE II

| | |
|---|---|
| Triethyleneglycol-bis-methacrylate | 0.26 g |
| Ingacure 651 (benzildimethylketal) | 0.19 g |
| Acrylic Acid | 37.5 g |
| Glycerin | 62.5 g |
| Water | 12.4 g |
| KOH | 12.4 g |

-continued

| coating thickness | | 3.2 mils (0.08 mm) |
|---|---|---|
| % R.H. | Impedence Z (Ω) | Adhesion to Steel (oz/in) |
| 5% | 6.4 | 10 no transfer |
| 50% | 1.5 | 4 no transfer |
| 80% | 1.4 | 3 slight transfer |

EXAMPLE III

| Triethyleneglycol-bis-methacrylate | 0.35 g |
|---|---|
| Irgacure 651 (benzildimethylketal) | 0.35 g |
| Acrylic Acid | 70.0 g |
| Glycerin | 130.0 g |
| Water | 19.0 g |
| KOH | 19.0 g |
| coating thickness | 3.3 mils (0.08 mm) |

| % R.H. | Impedence Z (Ω) | Adhesion to Steel (oz/in) |
|---|---|---|
| 5% | 8.6 | 5.5 no transfer |
| 50% | 2.0 | 4.0 no transfer |
| 80% | 1.1 | 3.5 transfer |

Example IV same adhesive precurser as Example III, different coating thickness, coating thickness 13.2 mils (0.33 mm):

| % R.H. | Impedence Z (Ω) | Adhesion to Steel (oz/in) |
|---|---|---|
| 5% | 120 | 9 no transfer |
| 50% | 7.8 | 5 no transfer |
| 80% | 1.9 | 5 slight transfer |

EXAMPLE V

| Triethylene glycol-bis-methacrylate | 0.20 g |
|---|---|
| Irgacure 651 (benzildimethylketal) | 0.20 g |
| Acrylic Acid | 40.0 g |
| Glycerin | 60.0 g |
| Water | 10.9 g |
| KOH | 10.9 g |
| coating thickness | 9.3 mils (0.24 mm) |

| % R.H. | Impedence Z (Ω) | Adhesion to Steel (oz/in) |
|---|---|---|
| 5% | 90 | 9 no transfer |
| 50% | 4.1 | 2 no transfer |
| 80% | 1.9 | 5.5 no transfer |

EXAMPLE VI

| Triethyleneglycol-bis-methacrylate | 0.18 g |
|---|---|
| Irgacure 651 (benzildimethylketal) | 0.1 g |
| Acrylic Acid | 23.5 g |
| Glycerin | 50.0 g |
| Water | 7 g |
| KOH | 7 g |
| coating thickness | 11.0 mils (0.28 mm) |

| % R.H. | Impedence Z (Ω) | Adhesion to Steel (oz/in) |
|---|---|---|
| 5% | NOT TESTED | |
| 50% | 6.4 | 2.5 no transfer |
| 80% | NOT TESTED | |

EXAMPLE VII

| Triethyleneglycol-bis-methacrylate | 0.18 g |
|---|---|
| Irgacure 651 (benzildimethylketal) | 0.18 g |
| Acrylic Acid | 35.0 g |
| Glycerin | 65.0 g |
| Water | 13.6 g |
| KOH | 13.6 g |
| coating thickness | 11.1 mils (0.28 mm) |

| % R.H. | Impedence Z (Ω) | Adhesion to Steel (oz/in) |
|---|---|---|
| 5% | 6.4 | 14 no transfer |
| 50% | 1.9 | 5 no transfer |
| 80% | 1.2 | 4.5 no transfer |

| Triethyleneglycol-bis-methacrylate | 0.04 g |
|---|---|
| Irgacure 651 (benzildimethylketal) | 0.18 g |
| Acrylic Acid | 35.0 g |
| Glycerin | 65.0 g |
| Water | 9.5 g |
| KOH | 9.5 g |
| coating thickness | 9.2 mils (0.23 mm) |

| % R.H. | Impedence Z (Ω) | Adhesion to Steel (oz/in) |
|---|---|---|
| 5% | 66 | 10 no transfer |
| 50% | 3.7 | 4.5 no transfer |
| 80% | 1.6 | 11 excessive transfer |

From Examples I through VIII, it can be seen that by varying the components of the precursor the conductivity and cohesive properties may be adjusted to suit the humidity conditions under which the conductive adhesive will be used. In the observation of the adhesion to steel, the term "transfer" was used herein to mean, slight adhesive residue was observed. It should be noted that the composition which exhibited some transfer when tested on steel did not leave adhesive residue on human skin. The useful conductivity level is largly dependent on the type of electrode on which the final polymer is applied. For example, in a ground plate electrode the conductivity is preferably less than 30 ohms at 50% (R.H.).

EXAMPLE IX

Preparation of Adhesive Precursor

Triethyleneglycol-bis-methacrylate (0.1 g) was dissolved in hdyroxyethylmethacrylate (10 g) and added to 50 grams of glycerol. The mixture was stirred and a solution of 0.1 gram benzildimethylketal dissolved in 15 grams of acrylic acid was added and mixed. A solution of potassium hydroxide (6.0 g) and water (10 ml) was then added. All components were combined within 10–15 minutes and then placed in a dark refrigerator to prevent premature polymerization. Test strips were then prepared in accordance with procedures outlined in Example I. An 11-mil (0.28 mm) thick layer of polymer at 50% relative humidity exhibited an impedance of 7.2 ohms and an adhesion of 1 oz/in.

EXAMPLE X

Preparation of Adhesive Precursor

Triethyleneglycol-bis-methacrylate (0.1 g) and 0.1 gram benzildimethylketal were dissolved in 32.5 grams of acrylic acid. This solution was rapidly added to 50 grams of glycerin. The mixture was stirred thoroughly and a solution of sodium hydroxide (5.0 g) and water (30 ml) was then added. All components were combined within 10–15 minutes and then placed in a dark refrigerator to prevent premature polymerization.

After the cooling of the precursor, test strips were prepared and tested as outlined in Example I. A test strip having an 11-mil (0.28 mm) thick polymer layer at 50% relative humidity exhibited an impedance of 9 ohms, and an adhesion of 8.5 oz/in.

EXAMPLE XI

Preparation of Adhesive Precursor

Triethyleneglycol-bis methyacrylate (0.1 g) and benzildimethylketal (0.1 g) were dissolved in 23.5 grams of acrylic acid. This solution was rapidly added to 50 grams of Sutro 970 (a mixture of polyols sold by ICI United States Inc. of Wilmington, Del.). The mixture was stirred thoroughly and a solution of potassium hydroxide (6 g) and water (10 g) was added. All components were combined within 10 to 15 minutes and then placed in a dark refrigerator.

After the cooling of the precursor, test strips were prepared and tested as outlined in Example I. A test sample having an 11-mil (0.28 mm) thick polymer layer at 50% relative humidity, exhibited an impedance of 200 ohms, and an adhesion of 1.5 oz/in.

What is claimed is:

1. A process for making an essentially dry biomedical electrode comprising of an electrode plate having a first surface and a second surface, means for electrically connecting said electrode plate to a lead wire of an electro-medical device, and a swellable, dermally-nonirritating, conformable, cohesive, ionic, hydrophilic polymeric conductive material on said second surface of said electrode plate for enhancing electrical connection with the skin, said process comprising: forming said conductive material on said electrode plate by the steps of:
   (a) compounding a precursor of said conductive material comprising
      (1) a water soluble polyhydric alcohol which is a liquid at about 20° C.;
      (2) an ionic, unsaturated, free radically polymerizable material soluble in said polyhydric alcohol;
      (3) a photo initiator; and
      (4) a crosslinking agent of a multi-functional unsaturated free radically-polymerizable material;
   (b) coating said precursor on said second surface of said electrode plate or onto a releasable transfer sheet; and
   (c) polymerizing said coated precursor by exposure to ultraviolet light whereby an electrically conductive pressure-sensitive adhesive layer is formed on said electrode plate or said transfer sheet; and
   (d) if formed on said transfer sheet, adhering said adhesive layer to said second surface of said electrode plate.

2. A process for making an essentially dry biomedical electrode comprising of an electrode plate having a first surface and a second surface, means for electrically connecting said electrode plate to a lead wire of an electromedical device, and a swellable, dermally-nonirritating, conformable, cohesive, ionic, hydrophilic polymeric conductive material on said second surface of said electrode plate for enhancing electrical connection with the skin, said process comprising: forming said conductive material on said electrode plate by the steps of:
   (a) compounding a precursor of said conductive material comprising:
      (1) a water-soluble polyhydric alcohol which is a liquid at about 20° C.;
      (2) acrylic acid, at least 10 percent of which has been neutralized to form a salt soluble in said polyhydric alcohol;
      (3) a photo-initiator; and
      (4) a crosslinking agent of a multifunctional unsaturated free radically polymerizable material which is soluble in said polyhydric alcohol;
   (b) coating said precursor on said second surface of said electrode plate or onto a releasable transfer sheet; and
   (c) polymerizing said coated precursor by exposure to ultraviolet light whereby an electrically conductive pressure-sensitive adhesive layer is formed on said electrode plate or said transfer sheet; and
   (d) if formed on said transfer sheet, adhering said adhesive layer to said second surface of said electrode plate.

3. The process according to claim 2 wherein said salt of acrylic acid is potassium acrylate or sodium acrylate.

4. The process according to claim 3 wherein said photo-initiator is benzildimethylketal.

5. The process according to claim 4 wherein paid precursor further comprises at least one non-ionic unsaturated free radically polymerizable monomer or comonomer which is soluble in said polyhydric alcohol.

6. The process according to claim 2 wherein said precursor further provides a tackifier.

7. The process according to claim 2 wherein said tackifier is polyacrylic acid.

8. A process for making an essentially dry biomedical electrode comprising of an electrode plate having a first surface and a second surface, means for electrically connecting said electrode plate to a lead wire of an electro-medical device, and a swellable, dermally-nonirritating, conformable, cohesive, ionic, hydrophilic polymeric conductive material on said second surface of said electrode plate for enhancing electrical connection with the skin, said process comprising: forming said conductive material on said electrode plate by the steps of:
   (a) compounding a precursor of said conductive material comprising:
      (2) a water-soluble polyhydric alcohol which is a liquid at about 20° C.;
      (2) an ionic unsaturated free radically polymerizable material which is soluble in said polyhydric alcohol;
      (3) a free radical initiator; and
      (4) a crosslinking agent of a multifunctional unsaturated free radically polymerizable material;
   (b) coating said precursor on said second surface of said electrode plate; and
   (c) polymerizing said coated precursor whereby an electrically conductive pressure-sensitive adhesive is formed on said electrode plate.

9. A process for making an essentially dry biomedical electrode comprising of an electrode plate having a first surface and a second surface, means for electrically connecting said electrode plate to a lead wire of an electromedical device, and a swellable, dermally-nonirritating, conformable, cohesive, ionic, hydrophilic polymeric conductive material on said second surface of said electrode plate for enhancing electrical connection with the skin, said process comprising: forming said conductive material on said electrode plate by the steps of:
(a) compounding a precursor of said conductive material comprising:
  (1) a water-soluble polyhydric alcohol which is a liquid at about 20° C;
  (2) an ionic unsaturate free radically polymerizable material which is soluble in said polyhydric alcohol;
  (3) a free radical initiator; and
  (4) a crosslinking agent of a multifunctional unsaturated free radically polymerizable material which is soluble in said polyhydric alcohol;
(b) coating said precursor onto a releasable transfer sheet;
(c) polymerizing said coated precursor whereby an electrically conductive pressure-sensitive adhesive is formed on said releasable transfer surface; and
(d) adhering said polymerized electrically-conductive material to said second surface of said electrode plate.

10. The process according to claim 8 wherein said precursor further comprises at least one non-ionic unsaturated free radically polymerizable monomer or comonomer which is soluble in said polyhydric alcohol.

11. The process according to claim 8 wherein said polyhydric alcohol is glycerol.

12. The process according to claim 11 wherein said ionic material is potassium acrylate.

13. The process according to claim 8 wherein said free radical initiator is a photoinitiator.

14. The process according to claim 9 wherein said precursor further comprises at least one non-ionic unsaturated free radially polymerizable monomer or comonomer which is soluble in said polyhydric alcohol.

15. The process according to claim 9 wherein said polyhydric alcohol is glycerol.

16. The process according to claim 15 wherein said ionic material is potassium acrylate.

17. The process according to claim 9 wherein said free radical initiator is a photoinitiator.

* * * * *

UNITED STATES PATENT AND TRADEMARK OFFICE
CERTIFICATE OF CORRECTION

PATENT NO. : 4,524,087

DATED : June 18, 1985

INVENTOR(S) : Michael R. Engel

It is certified that error appears in the above-identified patent and that said Letters Patent is hereby corrected as shown below:

Col. 3, line 41, "onjectionable" should be --objectionable--.

Col. 5, line 2, "is" should be --be--.

Col. 6, line 15, "178" should be --½--.

Col. 8, line 15, the heading --Example VIII-- should be inserted.

Col. 8, line 35, "mean," should be --mean a--.

Col. 9, line 29, "of" should be deleted.

Col. 9, line 60, "of" should be deleted.

Col. 10, line 36, "of" should be deleted.

Col. 10, line 62, "of" should be deleted.

Signed and Sealed this

Twenty-second Day of October 1985

[SEAL]

Attest:

DONALD J. QUIGG

Attesting Officer

Commissioner of Patents and
Trademarks—Designate